United States Patent [19]

Stadler et al.

[11] 3,997,593
[45] Dec. 14, 1976

[54] ORGANIC COMPOUNDS

[75] Inventors: Paul Stadler, Biel-Benken; Gernot Wersin, Locarno, both of Switzerland

[73] Assignee: Sandoz Ltd., Basel, Switzerland

[22] Filed: June 5, 1975

[21] Appl. No.: 583,884

[30] Foreign Application Priority Data

June 12, 1974 Switzerland .................. 8027/74

[52] U.S. Cl. .................. 260/484 P; 260/468 K
[51] Int. Cl.² .................. C07C 69/66
[58] Field of Search .................. 260/484 P, 468 K

[56] References Cited
UNITED STATES PATENTS

| | | | |
|---|---|---|---|
| 3,401,127 | 9/1968 | Stephenson | 260/484 P |
| 3,465,031 | 9/1969 | Stephenson | 260/484 P |
| 3,642,889 | 2/1972 | Platz et al. | 260/535 R |
| 3,705,922 | 12/1972 | Calligham | 260/535 R |

*Primary Examiner*—Paul J. Killos
*Attorney, Agent, or Firm*—Gerald D. Sharkin; Robert S. Honor; Thomas O. McGovern

[57] ABSTRACT

This invention provides a new process for the preparation of a compound of formula I,

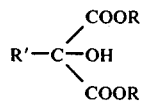

I wherein
R' is alkyl or cycloalkyl, and
R is an organic radical which is inert under the reaction conditions, by oxidizing a compound of formula II,

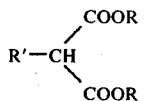

II wherein R and R' are as defined above, with nitric acid.

8 Claims, No Drawings

ORGANIC COMPOUNDS

The present invention relates to the production of esters.

In accordance with the invention there is provided a new process for the production of esters of formula I,

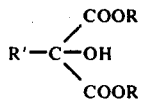

wherein
R' is alkyl or cycloalkyl, and
R is an organic radical which is inert under the reaction conditions,
by oxidizing a compound of formula II,

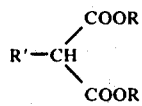

wherein R and R' are as defined above, with nitric acid. When alkyl, R' may contain from 1 to 6, preferably 1 to 4 carbon atoms. The process of the invention is especially suited for the production of compounds of formula I wherein R' is isopropyl.

R' may, for example, signify a cycloalkyl group of 3 to 6 carbon atoms.

R may be conveniently alkyl, preferably of 1 to 6 carbon atoms, e.g. methyl or ethyl.

It is convenient to use an excess of nitric acid. The nitric acid used in the process of the invention conveniently is at least 70 % nitric acid, the remainder containing at least some water. In accordance with a preferred method of this process 98 % to 100 % nitric acid is used. This dilution degree decreases risks of explosions. The excess of nitric acid preferably is not less than about 24 to 25 mols.

The nitric acid used as oxidizing agent dissolves the compounds of formula II well, so that the addition of a further inert solvent other than water may be superfluous.

The oxidation of compounds of formula II may be effected at temperatures between about 10° and 50° C, preferably 20° to 30° C. The reaction time may be about 6 hours to 2 days, depending on the % content and excess of nitric acid used and the reaction temperature, for a satisfactory yield.

The reaction mixture may be worked up in the usual manner, preferably by the addition of a large amount of water and subsequent extraction with a water-immiscible solvent which is inert under the extraction conditions. After concentrating the extract, the resulting crude product is purified in accordance with known methods, e.g. distillation in a high vacuum.

The process of the invention may, for example, be effected as follows: 1 mol of alkylmalonic acid ester is added dropwise at about 20° C to 26 mols of 98 % nitric acid, and the reaction mixture is kept at about 30° C for several hours. Working up is effected by diluting the reaction mixture with water and subsequently extracting with a water-immiscible solvent which is inert under the extraction conditions. The extract is subsequently washed, e.g. with a sodium hydrogen carbonate solution and water, is dried, the solvent is removed, and the residue purified, e.g. by high vacuum distillation.

The process of the invention is cheap, and may be readily carried out on a large scale to give satisfactory yields.

The compounds of formula II, used as starting materials, are known or may be produced in accordance with known methods.

The compounds of formula I are important basic products for the synthesis of e.g. ergot peptide alkaloids, such as, for example, ergotamine, and especially compounds of the ergotoxine series such as ergocornine, ergocristine, α- and β-ergocryptine, and the corresponding 9,10-dihydro derivatives, the valuable pharmacological properties of these compounds having been described in the literature. % refers to weight by weight.

In the following non-limitative Examples all temperatures are indicated in degrees Centigrade and are uncorrected.

EXAMPLE 1

Isopropyl-tartronic acid diethyl ester 1100 cc of 98 % nitric acid are placed in a 10-liter sulphonating flask provided with a stirrer, dropping funnel and thermometer, 202 g (1 mol) of isopropyl-malonic acid diethyl ester are added dropwise at 20° within one hour while stirring and cooling, and the resulting homogeneous solution is kept at 30° over night. Working up is effected by cooling the reaction mixture to 20°, and carefully diluting with 5 liters of water while cooling and stirring, whereby large amounts of nitrous gases escape. Immediately thereafter 2 liters of methylene chloride are added, and the mixture is stirred vigorously for 30 minutes. After removing the aqueous phase, the methylene chloride solution is diluted with 2 liters of water, is stirred for 20 minutes, and after separating the aqueous phase, the methylene chloride solution is washed in the same manner with one liter of a 5 % sodium hydrogen carbonate solution. The organic phase is again washed with water for a short time, dried with sodium sulphate, and the solvent is removed on a rotary evaporator. The resulting oil is separated by high vacuum distillation into two fractions which are further purified separately.

The main fraction which boils at 0.2 mm of Hg and between 60° and 75° is again rectified, whereby it yields isopropyl-tartronic acid diethyl ester as colourless oil having an apple-like odour. B.P. 64°–67°/0.3 mm of Hg. Purity determined by gas chromatography 94 %. $n_D^{22} = 1.4293$. The small last runnings having a higher boiling point are also distilled again in a high vacuum, whereby approx. 98 % (determined by gas chromatography) 2-isopropyl-2-nitromalonic acid diethyl ester is obtained. Colourless oil, $n_D^{20} = 1.4385$, B.P. 81°–82° (0.2 mm of Hg).

EXAMPLE 2

Isopropyl-tartronic acid diethyl ester 400 g (6.3 mols) of 98 % to 100 % nitric acid are placed in a sulphonating flask, and 10 g (0.05 mols) of isopropyl-malonic acid diethyl ester are added dropwise within 15 minutes at room temperature while stirring. The clear solution is allowed to stand at room temperature for 48 hours. Most of the nitric acid is then carefully removed by evaporation on a rotary evaporator under a water pump vacuum, the residue is distributed between an aqueous potassium hydrogen carbonate solution and a sufficient amount of methylene chloride and is worked up in the usual manner. The methylene chloride phases are again extracted with a small amount of water, dried over sodium sulphate, and the solvent is carefully removed by evaporation in a vacuum. The resulting crude product is distilled in a high vacuum and yields isopropyl-tartronic acid diethyl ester having a B.P. of 65°–67° (0.05 mm of Hg), $n_D^{20}=$ 1.4289.

The following compounds are obtained in a manner analogous to the processes described above:

| Produced compound | B.P. mm of Hg | $n_D^{20}$ |
|---|---|---|
| Methyl-tartronic acid diethyl ester | 59–60° (0.2) | 1.4230 |
| Ethyl-tartronic acid diethyl ester | 68–69° (0.5) | 1.4258 |
| n-Propyl-tartronic acid diethyl ester | 92–94° (1.3) | 1.4292 |
| n-Butyl-tartronic acid diethyl ester | 132–136° (13) | 1.4313 |
| Isobutyl-tartronic acid diethyl ester | 69–70° (0.2) | 1.4305 |
| Secondary-butyl-tartronic acid diethyl ester | 103–105° (1.5) | 1.4370 |

BACKGROUND OF THE INVENTION

Esters of formula I have hitherto been produced by quite laborious and expensive processes, e.g. using as starting material the expensive mesoxalic acid ester, which was alkylated with cadmium dialkylene [P. Freon and F. Tatebouet, C.r.hebd. Seances Acad. Sci. 249, 1361 (1959)], reacted with trialkyl phosphites in an Arbuzov reaction [A. N. Pudovik and J. V. Konovalova, Z. obsc. chim. 34, 3848 (1964); Chem. Abstr. 62, 9330 c] or condensed with α-olefins to alkyl-tartronic acid esters [O. Achmatowicz and O. Achmatovics, Roczniki Chem. 36, 1791 (1962); Chem. Abstr. 59, 8610 c]. Other processes used as starting materials the likewise considerably expensive α-ketonitriles and α-keto esters [N. Tschelinzeff and W. Schmidt, Ber. deutsch. Chem. Ges. 62, 2210 (1929); J. Cologne, L. Watteau and L. Cumet, Bull. soc. chim. France 1947, 245. See also A. Nenz, L. Marangoni, E. Galinella and A. Iliceto, Chim. Ind. (Milano) 46, 509 (1964); Chem. Abstr. 61, 4210] or production was effected via the alkyl-bromomalonic esters [W. Horsch and H. Probst, Arch. Pharmaz. 296, 249 (1963)] or acetoxy-malonic ester [K. C. Ghose, J. Indian Chem. Soc. 23, 311 (1946)].

It was also attempted to produce tartronic acid esters by direct oxidation of the very readily obtainable and thus cheaper alkyl-malonic acid esters. Oxidizing agents which have hitherto been used are: potassium permanganate/soda [S. Eskola and V. Moutinen, Suomen Kemistilethi 203B, 16 (1947); Chem. Abstr. 42, 123 a], lead tetraacetate [O. Dimroth and R. Schweizer, Ber. deutsch. Chem. Ges. 56, 1375 (1923); G. W. K. Cavill and D. H. Solomon, J. Chem. Soc. 1955, 4426], periodic acid [P. Fleury and J. Courtois, Bull. soc. chim. France 1947, 358] and tertiary-butyl or benzoyl peroxide [S. Lawesson, T. Busch and C. Berglund, Acta chem. scand. 15, 260 (1961)].

All these processes require expensive starting materials and/or reagents and/or give only low yields and, furthermore, their use cannot be generalized, so that a technical use of these processes for the production of compounds of formula I has great disadvantages.

The practicability of the present process, which may be readily used on a large technical scale, is surprising, since a treatment of alkyl-malonic acid esters with a mixture of fuming nitric acid/acetic anhydride [W. Steinkopf and A. Supan, Ber. deutsch. chem. Ges. 43, 3239 (1910)] or 100 % nitric acid/polyphosphoric acid [J. P. Kispersky and K. Klager, J. Amer. chem. Soc. 77 5433 (1955)] in each case only leads to the corresponding 2-nitro-2-alkyl-malonic acid esters, and a treatment of malonic acid esters with nitrous gases yields mesoxalic acid ester [Org. Synth. Collective volume 1, 266].

We claim:
1. A process for the production of a compound of formula I:

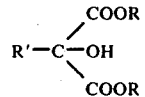

wherein
R' is alkyl of 1 to 6 carbon atoms or cycloalkyl of 3 to 6 carbon atoms, and
R is, alkyl of 1 to 6 carbon atoms
by oxidizing a compound of formula II,

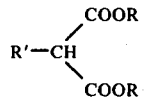

wherein R and R' are defined above, with nitric acid.

2. A process according to claim 1, wherein the nitric acid is present as an aqueous solution containing more than 70 % nitric acid.

3. A process according to claim 2, wherein the nitric acid is present as an aqueous solution containing more than 98 to 100 % nitric acid.

4. A process according to claim 1, wherein more than 24 mols of nitric acid per mol of the compound of formula II are present.

5. A process according to claim 1, carried out at a temperature of from 10° to 50° C.

6. A process according to claim 1, wherein R' is isopropyl.

7. A process according to claim 1, wherein R is methyl or ethyl.

8. A process according to claim 1 for the production of a compound of formula I:

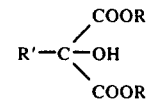

wherein
R' is isopropyl and
R is methyl or ethyl
which comprises oxidizing a compound of formula II:

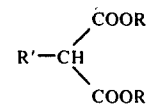

wherein R and R' are as defined above, with more than 4 moles of nitric acid per mole of the compound of formula II at a temperature of from 10° to 50° C.

* * * * *